(12) United States Patent
Pimentel

(10) Patent No.: US 7,344,713 B1
(45) Date of Patent: Mar. 18, 2008

(54) DECREASED FAT ABSORPTION WITH AN ANTI-LIPASE ANTIBODY

(76) Inventor: Julio L. Pimentel, 3206 Windgate Dr., Buford, GA (US) 30519

( * ) Notice: Subject to any disclaimer, the term of this patent is extended or adjusted under 35 U.S.C. 154(b) by 0 days.

(21) Appl. No.: 08/888,202

(22) Filed: Jul. 7, 1997

(51) Int. Cl.
*A61K 39/395* (2006.01)
*A61K 39/00* (2006.01)

(52) U.S. Cl. .............. 424/130.1; 424/146.1; 424/152.1; 424/157.1

(58) Field of Classification Search .............. 424/130.1
See application file for complete search history.

(56) References Cited

U.S. PATENT DOCUMENTS

| | | | | |
|---|---|---|---|---|
| 4,598,089 A | * | 7/1986 | Hadvary | 514/449 |
| 5,001,225 A | * | 3/1991 | Taylor | 530/388.6 |
| 5,080,895 A | * | 1/1992 | Tokoro | 524/130.1 |
| 5,585,098 A | * | 12/1996 | Coleman | 424/157.1 |
| 5,753,228 A | * | 5/1998 | Sterling et al. | |

FOREIGN PATENT DOCUMENTS

JP 02150294 * 6/1990

OTHER PUBLICATIONS

Moloney (Livestock Production Science, 42:239-245), 1995.*
Flint (Proceedings of the Nutrition Society, 51:433-439), 1992.*
Ohkaru et al (Clin. Chim. Acta, 182:295-300), 1989.*
Murase et al (Atherosclerosis, 39:293-300), 1981.*
Perryman et al (Infection and Immunity, 61:4906-4908), 1994.*
Martin et al (Am. J. Physiol., 266:G417-G424), 1994.*
Kelly et al (Antimicrobial Agents and Chemotherapy, Feb. 1997, 41:236-241).*
Bell, et al. The influence of energy density on satiation. The Faseb Journal (Abstracts) 11:A358. (1997).
Brodie, et al. "Fat reduction through the use of passive immunity" (Believed to be before Jul. 7, 1996).
Erhard, et al. New aspects in oral immunoprophylaxis. Berl. Munch. Tierarztl. Wschr. 106:383-387. (1993).
Flint, Immunological manipulation of adiposity. Proceedings of the Nutrition Society 51:433-439. (1992).
Gershoff, Nutrition evaluation of dietary fat substitutes. Nutrition Reviews 53:305-313. (1995).
Moloney, Immunomodulation of fat deposition. Livestock Production science 42:239-245. (1995).
Roy, et al. Metabolic effects of fat substitution with olestra. The Faseb Journal (Abstracts) 11:A358. (1997).
Shimizu, et al. Encapsulation of Chicken Yolk Immunoglobulin. Biosci. Biotech. Biochem 57:1445-1449. (1993).
Yokoyama, et al. Detection of passage and absorption of chicken egg yolk immunoglobulins. Am J. Vet Res. JY:867-872. (1993).
Brannon, et al. "Synthesis of Lipoprotein Lipase in Cultured Avian Granulosa Cells". Biochimica et Biophysica Acta, 531 (1978) 96-108.
Gershenwald, et al. "Monoclonal antibodies to avian lipoprotein lipase. Purification of the enzyme by immunoaffinity chromatography". Biochimica et Biophysica Acta, 836 (1985) 286-295.
Kurz, et al. "Plasma Apoprotein Changes after Selective Inhibition of Hepatic Triglyceride Lipase in Rat". (1984).
Drent, et al. "Lipase inhibition: a novel concept in the treatment of obesity". International Journal of Obesity (1993) 17:241-244.

* cited by examiner

*Primary Examiner*—Susan Ungar

(57) ABSTRACT

A method for the decrease of fat absorption in a mammal, wherein the animal is orally fed an antibody produced against lipase, an enzyme which is required for fat absorption.

7 Claims, No Drawings

DECREASED FAT ABSORPTION WITH AN ANTI-LIPASE ANTIBODY

BACKGROUND OF THE INVENTION

1. Field of the Invention

A food additive that decrease fat absorption in mammals

2. Discussion of the background

Our sedentary life including the decreased physical activity and increased food intake have made us prone to be overweight. The above has brought as consequence that almost 40-50% of the USA population is 20% above their desirable weight. The advance in the science of food and nutrition not only has made us wiser about the functions of all nutrients but also by applying that knowledge we have concentrated food in smaller portions by which the satisfaction of filling is decreased. Even if the amount of food intake remains the same, we will have an excess caloric intake due to the high energy concentration of such type of food (Bell, et al 1997). Currently, the weight loss related market is full of diet pills that reduce appetite by suppressing brain hormones, drugs that suppress the absorption of nutrients, pills that supposedly have ergogenics effect, pills that increase food passage rate and other fad diets. Mostly all of these drugs have secondary effects like depression, anxiety, addiction and others.

A new approach for the reduction of calories in food is by the use of fat substitutes (Gershoff, et al 1995). Each gram of fat provides 9 calories as compared to 4 calories per gram of carbohydrate and protein. Fat substitutes mainly those made of long carbohydrate chains are use for the elaboration of prepared food with the purpose of maintaining fat properties in the prepared food but decreasing calories. A new fat substitute, Olestra, which is made of long chain fatty acids that are too big for digestive enzymes (lipase) to breakdown, therefore that type of fat is not absorbed. It has been observed that the consumption of Olestra has resulted in decreased absorption of fat soluble and the presence of fat in the feces. A long term study (12 weeks) where ⅓ of the dietary fat was replaced with olestra, female subjects lost weight and did not compensate for the reduced calories and fat intake (Roy, et al, 1997).

In the animal industry, researchers have been working on the reduction of fat accumulation in animals since this characteristic first, has a negative effect on profits and second, consumers want less visible fat in order to decrease the health risk.

Fat accumulation in animals has been reduced by passively administered antibodies against adipocyte plasma membrane in rats, pigs, rabbits and lambs. Immunity against growth hormone has also decreased abdominal fat in chickens (Brodie and Hu, 1996; Moloney, 1995; Flint, 1992).

Lipase, an enzyme produced by the pancreas, hydrolyzes triacylglicerides into free fatty acids and glycerol. This is a crucial step in breaking down ingested fat in the gastrointestinal tract. Lipase is more active in the duodenum (small intestine) where broken down fat with the aid of bile salts form micelles and then are absorbed by the intestinal mucosa.

Therefore, by inhibiting lipase through binding the ingested fat will not be absorbed and the fat itself will be excreted.

SUMMARY OF THE INVENTION

A method for the inhibition of fat absorption in mammals.

DESCRIPTION OF THE PREFERRED EMBODIMENTS

The present invention relates to a method for decreasing fat absorption by orally feeding chicken antibodies against lipase to mammals, particularly post-suckling non-ruminant mammals. The preferred antigen for obtaining the antibodies is a swine pancreatic extract that contains lipase. This antigen is commercially produced by Sigma Chemical Co. Lipase is a conserve molecule with similar structure between animal and plant species, therefore an antibody against swine lipase will cross-react with other species' lipases. We have found that by feeding anti-lipase antibodies to post-suckling mice and rats will result in either decreased body weight or reduced feed efficiency. The antibody extract can either be fed in water suspension, included in feed as dry powder and/or encapsulated in liposomes.

Previous research on the effectiveness of chicken antibodies has been reported; i.e. the prevention of bacterial infection in swine, calf and dairy cows (Yokoyama et al, 1993; Erhard et al 1993; Coleman, 1995). These researches have also demonstrated the presence of intact avian antibodies in the gastro-intestinal tract of the animals.

Although chickens antibodies are known to protect against bacterial infections, no antibody has been reported to decreased fat absorption.

It will be apparent for those skilled in the art that the aforementioned objects and other advantages may be further achieved by the practice of the present invention.

EXAMPLE 1

This example illustrate the preparation of the specific antibody against lipase. 17-week old hens were injected with 2.5 mg of lipase (Sigma Chemical Co.). The inoculum was prepared by dissolving the enzyme in 0.2 ml phosphate buffered saline (PBS, pH 7.3) and 0.2 ml complete Freund's adjuvant. The antigen preparation was injected into two sites 0.2 ml in each (right and left) pectoralis muscle. A total of 0.4 ml of antigen preparation per hen was administered. A second injection was administered 5-6 weeks following the initial injection (at about 50% egg hen production). In the second antigen preparation, incomplete Freund's adjuvant was used instead of complete Freund's adjuvant. Hens were re-injected with the antigen preparation every two months or when the antibody titer was determined to be low. Antibody titer was determined by ELISA. Hens had free access to fed and water and they were maintained in an isolated room in order to minimized outside contamination.

EXAMPLE 2

Antibody was purified as follows: One volume of egg yolk of example 1 was mixed with 9 volumes of distilled water and left to sit overnight at 4° C. Then the aqueous portion was centrifuged at 4000 rpm for 10 minutes and filtered through a cheesecloth in order to remove any excess fat. The aqueous portion contains all the protein present in the egg yolk which includes all the antibodies (IgY). The liquid was frozen and then was freeze dried. The antibody activity was determine by ELISA.

EXAMPLE 3

Antibody against lipase was determined as follows:

1.—ELISA plates were coated with 100 ul lipase preparation (50 ug/ml) in carbonate buffer. The plates were incubated at 4° C. overnight prior to blocking with 1.5% bovine serum albumin for 4 hours at room temperature.

2.—100 ul of a 0.5 mg protein/ml antibody extract was added to each well and the plates incubated at room temperature for 1 hour.

3.—Plates were washed with PBS-tween solution. 100 ul of rabbit anti-chicken IgG conjugated to horseradish peroxidase was added to each well. The plates were incubated at room temperature for 1 hour.

4.—Plates were washed with PBS-tween and 100 ul of TMB substrate was added to each well and incubated for 15 minutes.

5.—The reaction was stopped with 100 ul of 2 M sulfuric acid.

6.—Plates were read at 455 nm in an ELISA plate reader.

7.—Titer was determine as the inverse of the dilution at which O.D. of the immunized egg was similar to the unimmunized control (O.D. <0.100).

EXAMPLE 4

This study illustrates the in vitro inhibition of lipase by the chicken anti-lipase antibody. The effectiveness of the antibody was verified by using a test specific for the determination of lipase in serum (Sigma Chemical Co). We modified this test by adding a known amount of enzyme (lipase) and antibody to a certain volume of phosphate buffered saline. The resulting activity was expressed as Sigma-Tietz units/ml, which is equal to the ml of 0.05 N NaOH required to neutralize the fatty acid formed in the reaction. In a preliminary study we found the following:

| Lipase (mg) | anti-lipase (protein extract) (mg) | Lipase Activity (U) | % decreased activity |
|---|---|---|---|
| 2.0 | 0 | 17.3 | |
| 2.0 | 9.0 | 18.8 | 0 |
| 1.0 | 0 | 14.0 | |
| 1.0 | 9.0 | 12.5 | 11 |
| 0.5 | 0 | 10.4 | |
| 0.5 | 9.0 | 9.8 | 6 |
| 0.25 | 0 | 8.1 | |
| 0.25 | 9.0 | 6.7 | 17 |

In a second test; higher amount of antibody extract was used. The results are as follows:

| Lipase (mg) | Anti-lipase Protein Extract (mg) | Lipase Activity (U) | % decreased activity |
|---|---|---|---|
| 2.0 | 0 | 18.7 | |
| 2.0 | 37 | 14.0 | 25 |
| 1.0 | 0 | 13.5 | |
| 1.0 | 37 | 6.9 | 49 |

EXAMPLE 5

This study illustrates the effect of anti-lipase antibody in mice. Two groups of 5 2-month old (i.e., post-suckling) mice (25-34 gr each) were given 5 mg of antibody (protein extract) per ml of water. The antibody was mixed with water on a daily basis. Mice were fed the same amount of feed in both groups (approx. 5 gr/mice/day). The length of the experiment was 58 days. The results are as follows.

| | total* initial body weight (gr) | total final body weight (gr) | difference in body weight (gr) | total feed intake (gr) | gr of feed needed to gain 1 gr of body weight |
|---|---|---|---|---|---|
| control | 157 | 199 | 42 | 1039 | 24.74 |
| anti-lipase | 156 | 187 | 31 | 1039 | 33.52 |

*Sum of 5 mice/trt

It will be apparent to those skilled in the art that a number of modifications and variations may be made without departing from the scope of the present invention as set forth in the appended claims.

REFERENCES

1.—Bell, E. A.; V. A. Castellanos; C. L. Pelkman; M. L. Thorwart and B. J. Rolls (1997). The influence of energy density on satiation. The Faseb Journal (Abstracts) 11:A358.

2.—Brodie A. and C. Y. Hu, (199) "Fat reduction through the use of passive immunity" in Biology of fat in meat animal.

3.—Coleman, M. (1996). Oral administration of chicken yolk immunoglobulins to lower somatic cell count in the milk of lactating ruminants. U.S. Pat. No. 5,585,098.

4.—Erhard, N. H., J. Kellner, J. Eichelberger and U. Losch (1993). New aspects in oral immunoprophylaxis for the prevention of infectious diarrhea newborn calves-a field study with specific egg antibodies. Berl. Munch. Tierarztl. Wschr. 106:383-387.

5.—Flint, David J. (1992) Immunological manipulation of adiposity. Proceedings of the Nutrition Society 51: 433-439.

6.—Gershoff, S. N. (1995). Nutrition evaluation of dietary fat substitutes. Nutrition Reviews 53:305-313.

7.—Moloney, A. P. (1995) Immunomodulation of fat deposition. Livestock Production science 42: 239-245.

8.—Roy, H.; J. Lovejoy; M. Windhauser and G. Bray (1997). Metabolic effects of fat substitution with olestra. The Faseb Journal (Abstracts) 11:A358.

10.—Shimizu, M.; Y. Miwa; K. Hashimoto and A. Goto (1993) Encapsulation of Chicken Yolk Immunoglobulin G (IgY) by liposomes. Biosci. Biotech. Biochem 57: 1445-1449.

11.—Yokoyama, H., R. Peralta, S. Serdo, Y. Ikemori (1993). Detection of passage and absorption of chicken egg yolk immunoglobins in the gastrointestinal tract of pigs by the use of enzyme-linked immunosorbent assay and fluorescent antibody testing. Am. J. Vet. Res. JY:867-872.

What is claimed is:

1. A method for decreasing mammalian absorption of fats by the gastrointestinal tract said method comprising inhibiting lipase activity in the mammal, said method comprising the step of: orally administering to the mammal anti-lipase avian antibodies that decrease activity of said lipase relative to a control, wherein said control does not receive said avian antibodies, wherein said inhibiting decreases the breaking down of ingested fats thereby decreasing the absorption of said fats by the gastrointestinal tract.

2. The method of claim 1, wherein prior to the step of administering to the mammal said avian antibody, said avian antibody is produced in avian eggs.

3. The method of claim 1, wherein prior to the step of administering said avian antibody, said avian antibody is first freeze dried or spray dried.

4. The method of claim 1, wherein said avian antibody is fed in a powder form or in liquid form admixed in whole egg or yolk.

5. The method of claim 1, wherein said avian antibody is fed in a liquid form.

6. A method of reducing weight gain in a mammal by decreasing mammalian absorption of fats in gastrointestinal tract by inhibiting lipase activity in said mammal, said method comprising the step of: orally administering to said mammal an amount of antilipase avian antibodies effective to decrease activity of said lipase relative to control, wherein said control does not receive said avian antibodies, wherein said inhibiting decreases the breaking down of ingested fats thereby decreasing the absorption of said fats by the gastrointestinal tract and reducing weight gain in said mammal.

7. The method of claim 6 wherein said step of orally administering comprises orally administering said antilipase antibody in combination with the mammal's feed.

* * * * *